United States Patent [19]
Routh et al.

[11] Patent Number: 5,735,881
[45] Date of Patent: Apr. 7, 1998

[54] VARIABLE ATRAIL BLANKING PERIOD IN AN IMPLANTABLE MEDICAL DEVICE

[75] Inventors: Andre Routh, Lake Jackson, Tex.; Annette Bruls, Brussels, Belgium; Craig Housworth, Lake Jackson; Joseph Vandegriff, Brazoria, both of Tex.; Yves Verboven, Kessel-lo, Belgium

[73] Assignee: Sulzer Intermedics Inc., Angleton, Tex.

[21] Appl. No.: 843,225

[22] Filed: Apr. 14, 1997

[51] Int. Cl.$^6$ ........................................... A61N 1/365
[52] U.S. Cl. ................................................. 607/14
[58] Field of Search .............................. 607/9, 14

[56] References Cited

U.S. PATENT DOCUMENTS

| | | | |
|---|---|---|---|
| 4,527,568 | 7/1985 | Rickards. | |
| 4,663,701 | 5/1987 | Stotts | 363/60 |
| 4,856,523 | 8/1989 | Sholder et al.. | |
| 4,903,699 | 2/1990 | Baker, Jr. et al.. | |
| 4,913,145 | 4/1990 | Stotts. | |
| 5,052,388 | 10/1991 | Sivula et al.. | |
| 5,103,819 | 4/1992 | Baker et al.. | |
| 5,190,052 | 3/1993 | Schroeppel. | |
| 5,350,409 | 9/1994 | Stoop et al. | 607/17 |
| 5,391,189 | 2/1995 | van Krieken et al. | 607/17 |
| 5,431,693 | 7/1995 | Schroeppel | 607/28 |
| 5,443,485 | 8/1995 | Housworth et al. | 607/28 |
| 5,543,795 | 8/1996 | Fernald | 341/163 |
| 5,571,144 | 11/1996 | Schroeppel | 607/28 |

OTHER PUBLICATIONS

Larry J. Stotts; Introduction to Implantable Biomedical IC Design; 1989; pp. 12–19; IEEE Circuits and Devices Magazine.

*Primary Examiner*—Scott M. Getzow
*Attorney, Agent, or Firm*—John R. Merkling

[57] ABSTRACT

An implantable medical device for electrically stimulating the heart to beat including a pulse generator, a logic and control unit, and an atrial sense circuit. The atrial sense circuit processes signals from electrodes implanted in an atrial chamber of the heart. The atrial sense circuit provides an atrial sense signal to the logic and control unit when the magnitude of electrical activity in the atria exceeds a threshold. The medical device preferably paces the ventricles in response to detected electrical activity in the atria indicative of atrial contraction. Immediately following ventricular pacing, the medical device initiates an absolute atrial blanking period followed by an atrial sensing period and a programmable blanking period. During both the absolute atrial blanking period and the programmable blanking period, atrial sensing is disabled, while during the atrial sense period, atrial sensing is enabled. The time durations of the atrial sensing period and the programmable blanking period are programmable and may be programmed noninvasively while the medical device is implanted. The time durations of the atrial sense period and the programmable blanking period are adjusted so that paced far field R-waves resulting from a ventricular pace preferably occur during the programmable blanking period when atrial sensing is disabled. Atrial sensing during the atrial sensing period advantageously allows the medical device to monitor the atrial sense signal for normal atrial contractions.

11 Claims, 4 Drawing Sheets

VARIABLE ATRAIL BLANKING PERIOD IN AN IMPLANTABLE MEDICAL DEVICE

BACKGROUND OF THE INVENTION

A. Field of the Invention

The present invention relates generally to cardiac stimulating devices, such as pacemakers and defibrillators. More particularly, the present invention relates to a cardiac stimulating device that detects electrical activity in the heart. Still more particularly, the present invention relates to a cardiac stimulating device that can distinguish normal heart beats from paced far field R-waves.

B. Description of the Related Art

In the normal human heart, illustrated in FIG. 1, the sinus (or sinoatrial (SA)) node generally located near the junction of the superior vena cava and the right atrium constitutes the primary natural pacemaker by which rhythmic electrical excitation is developed. The cardiac impulse arising from the sinus node is transmitted to the two atrial chambers (or atria) at the right and left sides of the heart. In response to excitation from the SA node, the atria contract, pumping blood from those chambers into the respective ventricular chambers (or ventricles). The impulse is transmitted to the ventricles through the atrioventricular (AV) node, and via a conduction system comprising the bundle of His, or common bundle, the right and left bundle branches, and the Purkinje fibers. The transmitted impulse causes the ventricles to contract, the right ventricle pumping unoxygenated blood through the pulmonary artery to the lungs, and the left ventricle pumping oxygenated (arterial) blood through the aorta and the lesser arteries to the body. The right atrium receives the unoxygenated (venous) blood. The blood oxygenated by the lungs is carried via the pulmonary veins to the left atrium.

This action is repeated in a rhythmic cardiac cycle in which the atrial and ventricular chambers alternately contract and pump, then relax and fill. Four one-way valves, between the atrial and ventricular chambers in the right and left sides of the heart (the tricuspid valve and the mitral valve, respectively), and at the exits of the right and left ventricles (the pulmonic and aortic valves, respectively, not shown) prevent backflow of the blood as it moves through the heart and the circulatory system.

The sinus node is spontaneously rhythmic, and the cardiac rhythm originating from the primary natural pacemaker is termed normal sinus rhythm ("NSR") or simply sinus rhythm. This capacity to produce spontaneous cardiac impulses is called rhythmicity, or automaticity. Some other cardiac tissues possess rhythmicity and hence constitute secondary natural pacemakers, but the sinus node is the primary natural pacemaker because it spontaneously generates electrical pulses at a faster rate. The secondary pacemakers tend to be inhibited by the more rapid rate at which impulses are generated by the sinus node.

Disruption of the natural pacemaking and propagation system as a result of aging or disease is commonly treated by artificial cardiac pacing, by which rhythmic electrical discharges are applied to the heart at a desired rate from an artificial pacemaker. An artificial pacemaker (or "pacer" as it is commonly labeled) is a medical device which delivers electrical pulses to an electrode that is implanted adjacent to or in the patient's heart in order to stimulate the heart so that it will contract and beat at a desired rate. If the body's natural pacemaker performs correctly, blood is oxygenated in the lungs and efficiently pumped by the heart to the body's oxygen-demanding tissues. However, when the body's natural pacemaker malfunctions, an implantable pacemaker often is required to properly stimulate the heart. An in-depth explanation of relevant cardiac physiology and pacemaker theory of operation is provided in U.S. Pat. No. 4,830,006.

Pacers today are typically designed to operate using one of three different response methodologies, namely, asynchronous (fixed rate), inhibited (stimulus generated in absence of a specified cardiac activity), or triggered (stimulus delivered in response to a specified hemodynamic parameter). Broadly speaking, the inhibited and triggered pacemakers may be grouped as "demand" type pacemakers, in which a pacing pulse is only generated when demanded by the heart. To determine when pacing is required by the pacemaker, demand pacemakers may sense various conditions such as heart rate, physical exertion, temperature, and the like. Moreover, pacemakers range from the simple fixed rate, single chamber device that provides pacing with no sensing function, to highly complex models that provide fully automatic dual chamber pacing and sensing functions. The latter type of pacemaker is the latest in a progression toward physiologic pacing, that is, the mode of artificial pacing that most closely simulates natural pacing.

Because of the number of options available for pacer operation, an industry convention has been established whereby specific pacer configurations are identified according to a code comprising three, four or five letters. The fifth code position describes the antitachycardia functions, if any. Because this position is not applicable to most commonly used pacemaker types, most common codes comprise either three or four letters as shown in the table below. For this reason and for simplicity's sake, the fifth code position is omitted from the following table. Each code can be interpreted as follows:

|  | Code position | | | |
| --- | --- | --- | --- | --- |
|  | 1 | 2 | 3 | 4 |
|  | Function identified | | | |
|  | chamber paced | chamber sensed | response to sensing | programmability, rate modulation |
| Options available | 0—none<br>A—atrium<br>V—ventricle<br>D—dual<br>(A + V) | 0—none<br>A—atrium<br>V—ventricle<br>D—dual<br>(A + V) | 0—none<br>T—triggered<br>I—inhibited<br>D—dual<br>(T + I) | 0—none<br>P—programmable<br>M—multi-programmable<br>C—communicating<br>R—rate modulating |

For example, patients experiencing either atrial bradyarrythmias with or without A-V block or normal sinus rhythm with A-V block preferably use a DDD pacer. A DDD pacer paces either chamber (atrium or ventricle) and senses in either chamber. Thus, a pacer in DDD mode, may pace the ventricle in response to electrical activity sensed in the atrium. By pacing the ventricle in response to atrial activity (resulting from or occurring during atrial contraction), proper synchronization is maintained between the atria and ventricles and blood is efficiently pumped through the circulatory system. Moreover, for DDD mode pacers to function properly, accurate detection of atrial contractions is required.

Accurate detection of true atrial activity may be impaired by ventricular pacing in a DDD pacer. After a ventricular pace, the atrial sense amplifier can detect three separate events: (1) the ventricular pacing pulse; (2) the far-field R-wave (FFRW) caused by the depolarization of the large ventricular muscle mass which creates a signal large enough to be seen in the atria; and (3) retrogradely conducted activity caused by electrical conduction from the ventricle.

After a ventricular pace, an atrial refractory period called post ventricular atrial refractory period (PVARP) is initiated, and is typically 250–350 milliseconds. PVARP is further divided into absolute and relative portions. The absolute portion, which may also be called post ventricular atrial blanking (PVAB), typically 100–150 msec, functions to blank out the ventricular pacing spike. The relative portion of PVARP is opened up to atrial sensing, but not tracking. Atrial events sensed in this portion will be logged for diagnostic purposes to sense Premature Atrial Contractions (PAC's) or retrograde conduction which would otherwise be undetected if the PVARP were totally blanked. This relative atrial sensing portion is susceptible, however, to sensing a FFRW from the ventricle. Such a FFRW would falsely be interpreted as having an atrial origin. Operations, such as mode switching algorithms, which depend on atrial sensing would then have erroneous input.

The sensing and timing of FFRWs sensed by the atrial sense amplifier is highly variable among patients because of different heart geometries, lead placements, programmed atrial sensitivity, and other factors. Retrograde conduction may also vary between patients, particularly after premature ventricular beats.

In an attempt to overcome the problem of longer time periods between ventricular pacing and detection of the paced FFRW in the atria, some pacers include a programmable PVARP. These pacers allow the PVARP to be programmed uniquely for each patient.

Programming the PVARP to longer time periods, however, creates an additional problem. It is possible that during the PVARP the atria may naturally contract as a result of normal SA node behavior. The probability of normal atrial contractions occurring during the PVARP increases as the PVARP becomes longer in duration. Because atrial sensing is disabled during the PVARP, normal atrial activity is undetected. Consequently, pacemaker designers have struggled with trading off longer PVARP durations to ensure that paced FFRWs are rejected against shorter PVARP durations to ensure that normal atrial activity is detected.

It thus would be advantageous for a pacer to accurately distinguish paced FFRWs from normal atrial contractions. Such a system would only pace the ventricles in response to true atrial contractions, and not respond to FFRWs. Despite the advantages such a system would offer, to date no such system exists.

SUMMARY OF THE INVENTION

Accordingly, there is herein provided an implantable medical device such as a pacemaker for electrically stimulating the heart to beat and distinguish normal heart beats from paced far field R-waves. The medical device includes a pulse generator, a logic and control unit, and an atrial sense circuit. The atrial sense circuit processes signals from electrodes implanted in an atrial chamber of the heart. The atrial sense circuit provides an atrial sense signal to the logic and control unit when the magnitude of electrical activity in the atria exceeds a threshold often an indication of atrial contraction. The medical device paces the ventricles in response to detected electrical activity in the atria preferably indicative of atrial contraction.

Immediately following ventricular pacing, the medical device initiates an absolute atrial blanking period during which atrial sensing is disabled. Immediately following the absolute atrial blanking period, the medical device initiates an atrial sensing period during which atrial sensing is enabled. Upon expiration of the atrial sensing period, a programmable blanking period is enabled during which atrial sensing is again disabled. The time durations of the atrial sensing period and the programmable blanking period are programmable and may be programmed while the medical device is implanted. Both the atrial sensing period and the programmable blanking period are independently programmable in the range of approximately 0 to 100 milliseconds.

When the ventricles are paced by the medical device, the electrical pulse propagates through the ventricles and upwards into the atria and may be detected by the atrial electrodes. The blanking and sensing periods are provided to prevent the medical device from mischaracterizing the detected atrial signal, or paced far field R-wave, as indicative of normal atrial contraction. The time lag between the time the ventricular pacing and the time the paced far field R-wave is detected by the atrial electrodes varies from patient to patient, but is generally consistent for a given patient. Once the time lag is determined for the patient, the time durations of the atrial sense period and the programmable blanking period are adjusted so that all paced far field R-waves preferably occur during the programmable blanking period during which atrial sensing is disabled. Thus, the paced far field R-wave is not recognized by the invention and thus not mischaracterized as atrial contraction. Atrial sensing during the atrial sensing period advantageously allows the medical device to monitor the atrial sense signal for normal atrial contractions. Moreover, the advantage of a long post-ventricular atrial refractory period to reject paced far field R-waves is achieved, while reducing the risk of missing normal atrial contractions that may occur during the atrial refractory period.

BRIEF DESCRIPTION OF THE DRAWINGS

Other objects and advantages of the invention will become apparent upon reading the following detailed description and upon reference to the accompany drawings, wherein.

DETAILED DESCRIPTION OF THE INVENTION

Figure 1:
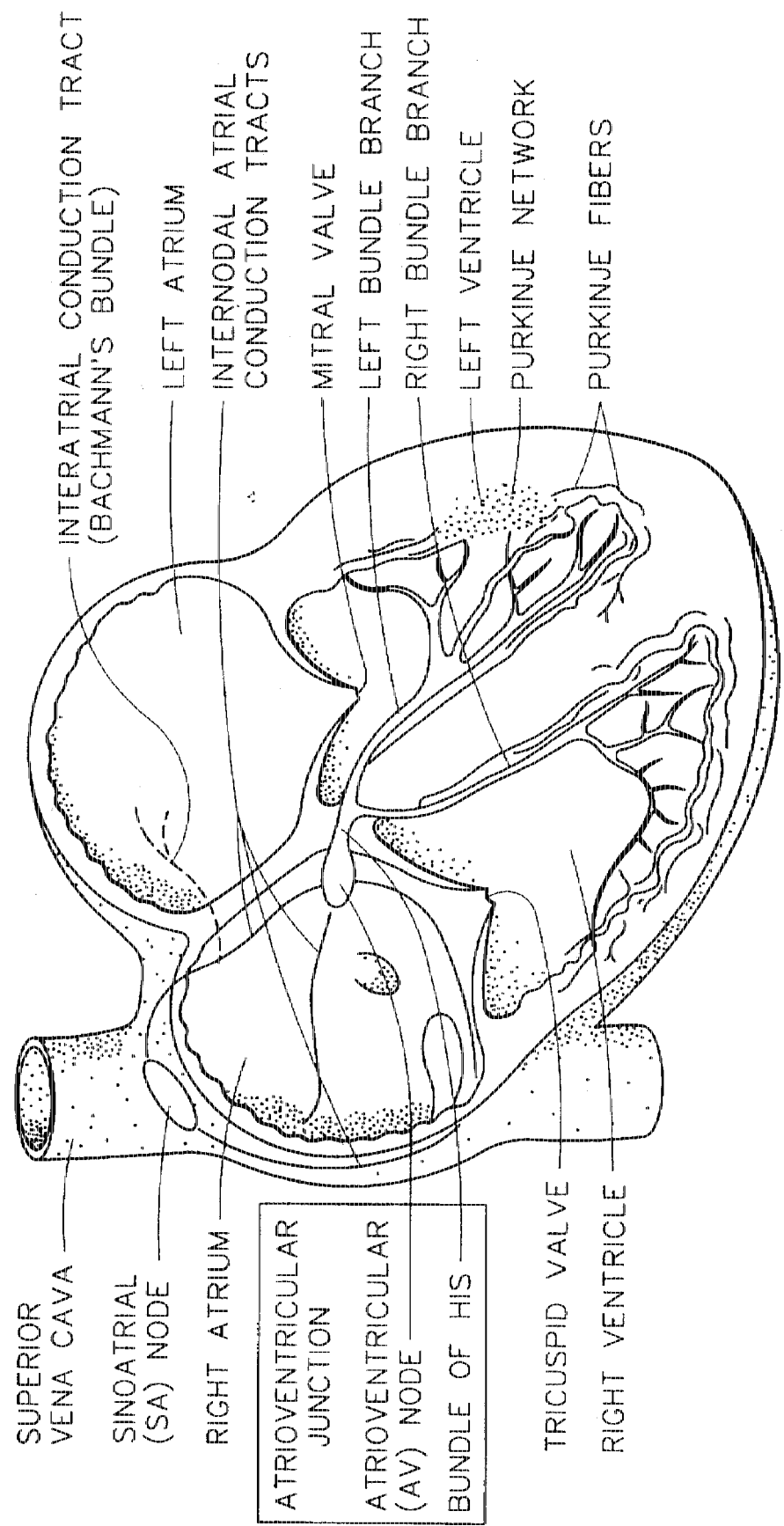
FIG. 1 is a schematic cut-away view of a human heart, in which the various relevant parts are labeled.
Figure 2:
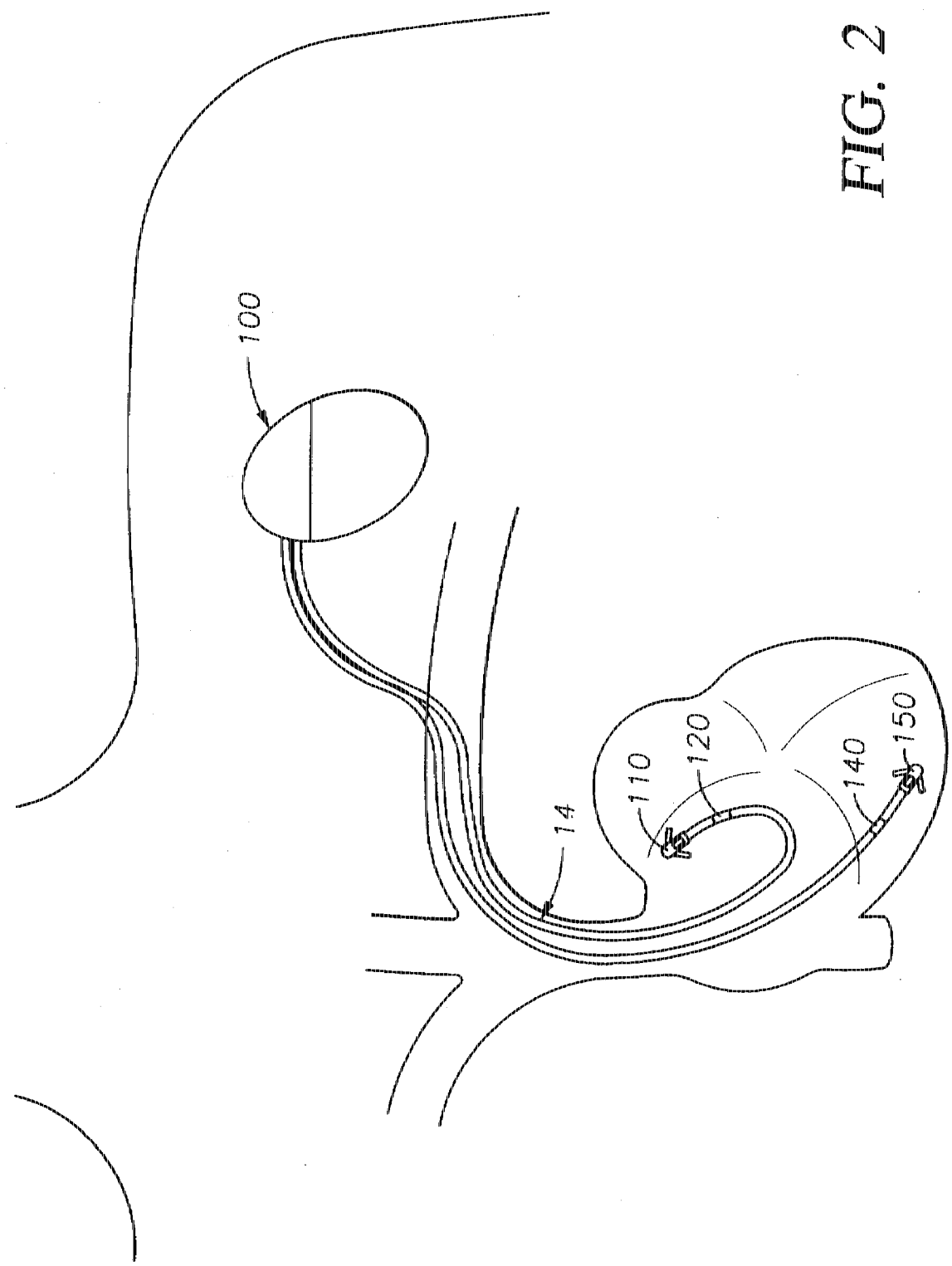
FIG. 2 is a schematic diagram of a dual-chamber pacer implanted in a human body.

Referring now to FIG. 2, an implantable medical device 100 constructed in accordance with the preferred embodiment is shown implanted and coupled to the patient's heart by leads 12, 14. The implantable medical device 100 may include a pacemaker or any medical device that performs pacing functions. For purposes of describing the preferred embodiments of the invention, the implantable medical device will hereafter be described as an implantable pacemaker or simply pacer 100. However, it should be understood that the invention may likewise be employed in any of a variety of implantable medical devices, such as defibrillators.

In the dual chamber pacing arrangement shown, leads 12, 14 are positioned in the right ventricle and right atrium, respectively. Alternatively, leads could be attached to the left ventricle and left atrium. Each lead 12, 14 includes at least one stimulating electrode for delivery of electrical impulses to excitable myocardial tissue in the appropriate chamber(s) in the right side of the patient's heart. As shown in FIG. 2, each lead 12, 14 includes two electrodes. More specifically, lead 14 includes tip electrode 110 and ring electrode 120, and lead 12 includes tip electrode 150 and ring electrode 140. As one skilled in the art will understand, two, three, and four terminal devices all have been used or suggested as possible electrode schemes and may be employed in the present invention.

Figure 3:
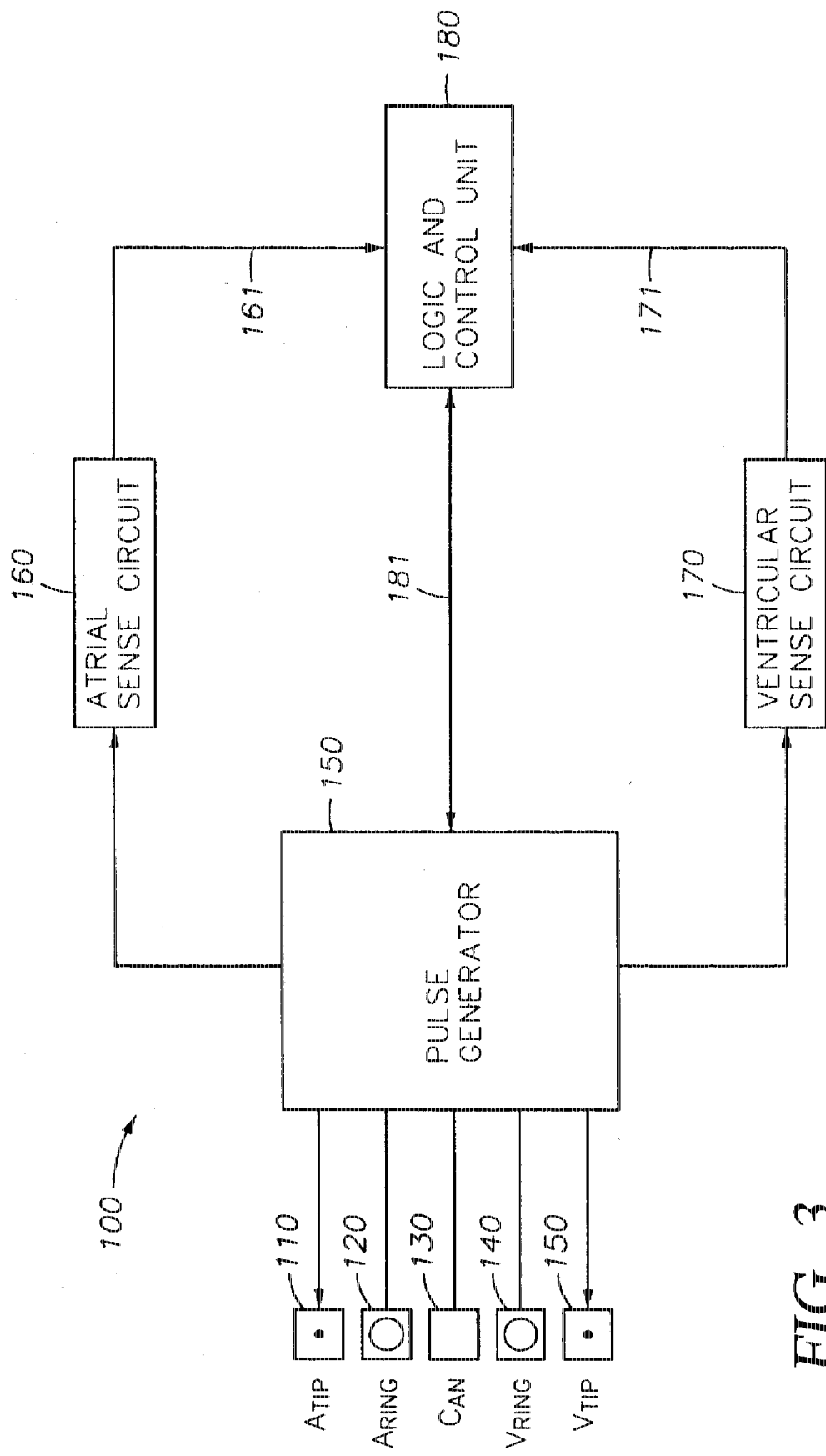
FIG. 3 is a block diagram of the pacer constructed in accordance with the present invention to provide an absolute atrial blanking period, atrial sense period, and a programmable blanking period.

Referring now to FIG. 3, an implantable medical device 100 constructed in accordance with the preferred embodiment is shown to include electrodes 110, 120, 130, 140, 150, pulse generator 150, atrial sense circuit 160, ventricular sense circuit 170, and logic and control unit 180. The implantable medical device 100 may include a pacemaker or any medical device that performs pacing functions. For purposes of describing the preferred embodiments of the invention, it will hereafter be described as an implantable pacemaker or simply pacer. However, it should be understood that the invention may likewise be employed in any of a variety of implantable medical devices, such as defibrillators.

Pulse generator 150 delivers pacing pulses to the heart generally through one or more electrodes 110, 120, 130, 140, 150. Pulse generators are well known in the art and typically include voltage multipliers, voltage regulators, rate limiters, and output switches. Pulse generator 150 preferably is capable of unipolar or bipolar pacing of either an atrium or ventricle. Pulse generator 160 is controlled by logic and control unit 180 via control lines 181. Logic and control unit 180 initiates pacing, determines the amplitude and pulse width of the pacing pulse, and provides that information to pulse generator 150 over control lines 181.

Atrial sense circuit 160 and ventricular sense circuit 170 preferably include a known low-power amplifier, band pass filter, and threshold detector (not specifically shown). Output switches (also not shown) in pulse generator 150 couple the sense circuits to a pair of electrodes. The sense circuits amplify the signal from the electrodes and attenuate extraneous noise and other undesired signals. The threshold detectors produce a sense signal when the magnitude of the signal from the electrodes exceeds a threshold level, thus indicating an atrial sense (AS) or ventricular sense (VS) event. Atrial sense circuit 160 provides an atrial sense signal on line 161 to logic and control unit 180 representative of an AS event. Similarly, ventricular sense circuit 170 provides a ventricular sense signal to logic and control unit 180 on line 171 representative of a VS event. Thus, logic and control unit 180 monitors lines 161,171 for AS and VS events.

Figure 4:
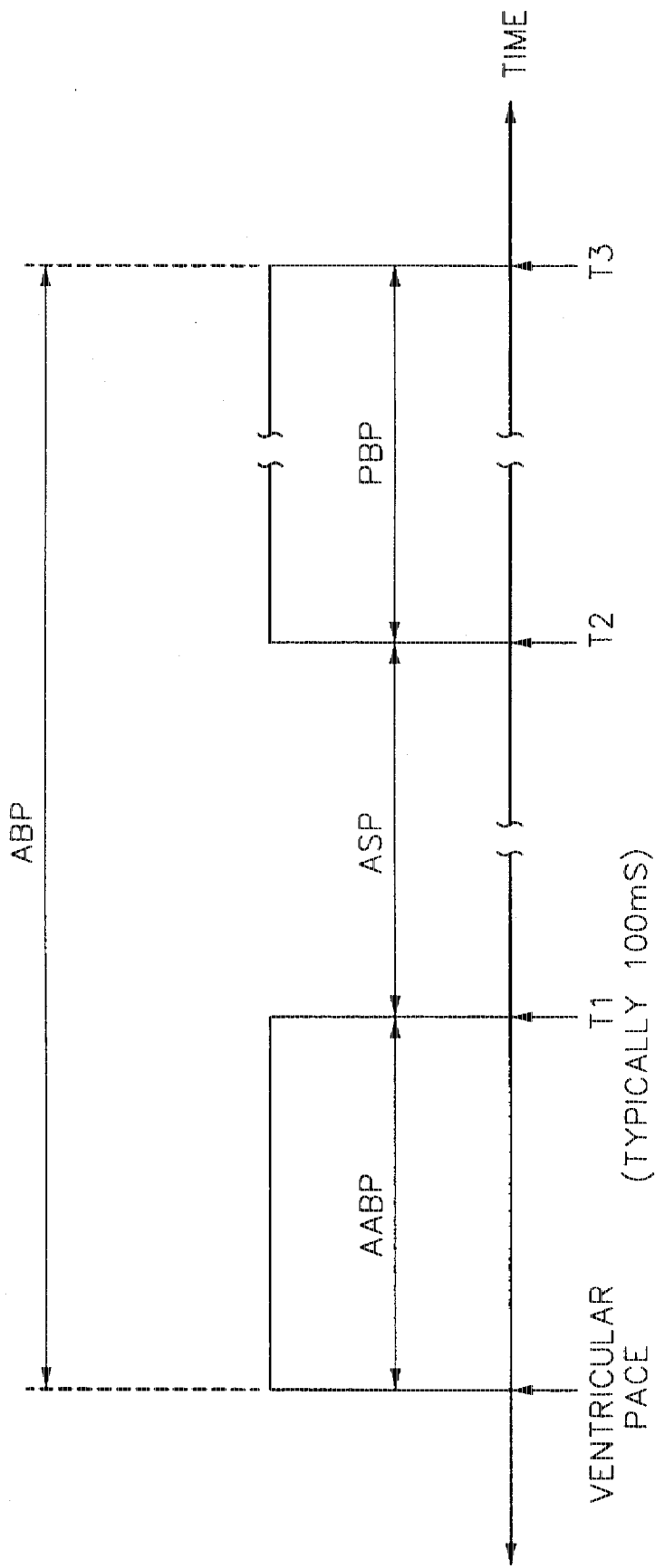
FIG. 4 shows the timing relationships between the absolute atrial blanking period, atrial sense period, and a programmable blanking period.

Pacer 100 may operate in any of a variety of operational modes. In those modes in which the ventricles are paced in response to a sensed atrial event, such as DDD mode, pacer 100 provides an atrial blanking period that includes an absolute atrial blanking period ("AABP"), atrial sense period ("ASP"), and a programmable blanking period ("PBP"). Referring now to FIG. 4, the AABP begins when pacer 100 paces the ventricles and ends after some predetermined time duration at point T1. AABP preferably is not adjustable and is 100 ms in duration. It should be recognized, however, that AABP may be more or less than 100 ms long.

During the AABP, pacer 100 generally disables its atrial sensing function, using any one of a variety of techniques. For example, logic and control unit 180 may simply ignore the atrial sense signal provided over line 161 from atrial sense circuit 160. Alternatively, the output switches in pulse generator 150 which connect the atrial electrodes to the atrial sense circuit 160, may be opened preventing electrical signals from the atrial electrodes from reaching atrial sense circuit 160. Beginning at point T1 and ending at point T2, pacer 100 begins the ASP in which the atrial sense function is enabled and the atrial sense signal is provided to logic and control unit 180 which monitors the sense signal for atrial electrical activity. Finally, following the atrial ASP, pacer 100 provides the PBP ending at point T3. Pacer operation during PBP is similar to the operation during AABP and the atrial sense function is again disabled. Following PBP, normal pacer operation resumes.

Although the time duration of AABP is fixed, the time durations of ASP and PBP are programmable during the implantation procedure and thereafter. Both ASP and PBP are programmable preferably in the range of 0 to 100 ms. Thus, the ASP and PBP periods may be non-existent (i.e., 0 ms in duration) or be as long as 100 ms.

Research has shown that the time lag between a ventricular pace and detection of the paced FFRW by the atrial electrodes and sense circuit varies from patient to patient as explained previously. However, for a given patient, the time lag is generally constant. Thus, it is intended that the time lag between a ventricular pace and atrial detection of a paced FFRW will be measured for a given patient and the time durations of ASP and PBP will be programmed accordingly. For example, if the time lag for a patient is 90 ms, both ASP and PBP may be programmed to 0 ms as the paced FFRW will occur during the AABP. However, for a time lag of 150 ms, ASP may be programmed to a value less than 50 ms. If ASP is programmed to 35 ms, for example, T2 (FIG. 4) occurs at 135 ms. In that case, PBP will begin at 135 ms after the ventricular pace occurs and is programmed to last at least 15 ms and preferably slightly longer to insure the PBP period includes the paced FFRW.

Thus, ASP and PBP are programmable to any duration commensurate with any time possible lag between ventricular pacing and paced FFRW detection by the atrial electrodes. Further, pacer 100 can be programmed during the implantation procedure and reprogrammed at any time thereafter, usually during a doctor visit. To that end, the time lag between ventricular pacing and detection of the paced FFRW can be measured by techniques known to those of ordinary skill in the art. During the initial or subsequent programming procedure, new ASP and PBP time duration values are transmitted to pacer 100 using known telemetry techniques such as transcutaneous energy transmission. The ASP and PBP time duration values, as well as other configuration values used for pacer operation, are stored in memory in pacer 100 (not shown in FIG. 3).

Moreover, by providing an intermediate time period, ASP, during which atrial sensing occurs, normal atrial activity can be monitored while pacer 100 also rejects paced FFRWs. Thus, the present invention solves the problem of previous pacers in which atrial contractions were not detected during long PVARPs.

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention.

Accordingly, the scope of protection is not limited to the embodiments described herein, but is only limited by the claims which follow, the scope of which shall include all equivalents of the subject matter of the claims.

What is claimed is:

1. A medical device for electrically stimulating the heart to contract and for distinguishing a normal heart beat from a paced FFRW, comprising:

a plurality of electrodes coupled to the heart;

a logic and control unit for initiating a pacing pulse to be delivered to the heart, said logic and control unit including memory for storing configuration values;

a pulse generator coupled to and controlled by said logic and control unit, said pulse generator delivering a pacing pulse to the heart through said plurality of electrodes;

a sense circuit disposed between said pulse generator and said logic and control unit for processing electrical activity detected in a chamber of the heart and providing a sense signal to the logic and control unit indicative of detected electrical activity in said chamber;

wherein said logic and control unit upon ventricular pacing initiates an absolute blanking period, said absolute blanking period followed by a sense period, said sense period followed by a programmable blanking period, wherein during said sense period the logic and control unit monitors said sense signal and during said absolute blanking period and said programmable blanking period the logic and control unit disables monitoring of said sense signal.

2. The medical device of claim 1 wherein said sense period includes a programmable first time duration.

3. The medical device of claim 2 wherein said programmable blanking period includes a programmable second time duration during which a paced FFRW occurs.

4. The medical device of claim 3 wherein said sense period is programmable in the range of approximately 0 milliseconds to 100 milliseconds.

5. The medical device of claim 4 wherein said programmable blanking period is programmable in the range of approximately 0 milliseconds to 100 milliseconds.

6. The medical device of claim 5 wherein said chamber includes an atrium.

7. A method for distinguishing a normal heart beat from a paced FFRW using an implantable medical device that includes an atrial sense circuit for processing electrical signals from an atrial chamber of the heart, comprising the steps of:

(a) pacing a ventricular chamber of the heart;

(b) initiating an absolute atrial blanking period upon pacing said ventricular chamber, wherein atrial sensing is disabled during said absolute atrial blanking period;

(c) initiating an atrial sense period of a first time duration upon expiration of said atrial blanking period, wherein atrial sensing is enabled during said atrial sense period; and (d) initiating a programmable blanking period of a second time duration upon expiration of said atrial sense period, wherein atrial sensing is disabled during said programmable blanking period.

8. The method of claim 7 wherein said first time duration is programmable.

9. The method of claim 8 wherein said second time duration is programmable.

10. The method of claim 9 wherein said first time duration is programmable in the range of approximately 0 to 100 milliseconds.

11. The method of claim 10 wherein said second time duration is programmable in the range of approximately 0 to 100 milliseconds.

* * * * *